United States Patent [19]

Wieczorek et al.

[11] 4,364,107

[45] Dec. 14, 1982

[54] METHOD AND DEVICE FOR USING MASS-PRODUCED LIGHT-EMITTING DIODES AT A PREDETERMINED LUMINANCE

[75] Inventors: Hanne-Lore Wieczorek; Adolf Triller, both of Munich; Helmut Gassenhuber, Söcking, all of Fed. Rep. of Germany

[73] Assignee: Optische Werke G. Rodenstock, Munich, Fed. Rep. of Germany

[21] Appl. No.: 172,948

[22] Filed: Jul. 28, 1980

[30] Foreign Application Priority Data

Jul. 26, 1979 [DE] Fed. Rep. of Germany ....... 2930405

[51] Int. Cl.³ .............................................. F21V 3/00
[52] U.S. Cl. .................................. 362/285; 362/311; 362/372; 362/455; 362/800
[58] Field of Search ................. 362/32, 800, 311, 285, 362/372, 455

[56] References Cited

U.S. PATENT DOCUMENTS 4,177,503 12/1979 Auquetin ............................ 362/252

*Primary Examiner*—Stephen J. Lechert, Jr.
*Attorney, Agent, or Firm*—Paul M. Craig, Jr.

[57] ABSTRACT

A method for using mass-produced light-emitting diodes of a predetermined luminance in instruments requiring a precise luminance value and a light-emitting diode arrangement for adapting such mass-produced light emitting diodes to such instruments. The above-noted method includes the steps of disposing an LED in a lengthwise adjustable manner within a sleeve, closing the sleeve with a light diffusing disc at an end thereof from which the light from the LED is intended to merge and displacing the LED within the sleeve in such a manner that a precisely defined luminance appears at the diffused disc. In accordance with a preferred embodiment of the apparatus, a tubular sleeve of an elastic plastic material is provided with mounting threads at one end thereof for mounting same within a cap with a light-diffusing disc located between the threaded end of the sleeve and the cap. Additionally, the sleeve is provided with longitudinally extending beads within which electrical connectors of the LED can be mounted. The LED is positionally adjustable with respect to the diffusing disc by elastic deformation of the sleeve and is held in place at a position to which it is adjusted by the force produced by the sleeve at an area of localized elastic deformation adjacent the LED.

9 Claims, 2 Drawing Figures

METHOD AND DEVICE FOR USING MASS-PRODUCED LIGHT-EMITTING DIODES AT A PREDETERMINED LUMINANCE

BACKGROUND AND SUMMARY OF THE INVENTION

The invention relates to a method as well as a device for using mass-produced light-emitting diodes (LEDs) of a predetermined luminance, preferably in ophthalmic testing equipment, for example as stimuli in hemispherical perimeters.

It is known for example from German Pat. No. 2,507,723, to use LEDs as stimuli in perimetric ophthalmic testing equipment.

A prerequisite for precise test results is a uniform luminance of the LEDs located on the hemispherical viewing area of the perimeter. Heretofore, LEDs with approximately the same luminance were selected from a plurality of LEDs. This method is uneconomical, and allows certain variations in the luminance of the selected LEDs. Likewise, similar, but lesser, requirements for uniform luminance occur in equipment where LED readouts are utilized in place of meters and guages, such as VU meters in stereo cassette decks, receivers, and the like.

Thus, an object of the present invention is to permit the use of mass-produced LEDs at a precisely predetermined luminance, as required for stimuli in hemispherical perimeters, with practically zero rejects.

The above noted object is achieved according to an apparatus aspect of the invention by an LED arrangement wherein the LED is longitudinally adjustably retained in an elastic plastic tube which is sealed at one end by a light diffusing disc, and according to a method aspect of the invention by the use of conventional LEDs in the noted arrangement to meet precision requirements by adjusting the distance between the LED and the diffusing disc until the precise required luminance is achieved.

An important feature of the displaceable arrangement is that a conventional mass-produced LED can be mounted in a sleeve that is closed at the end from which the light emerges by a diffusing disc without care being taken to select a LED of a particular luminance. To achieve a uniform luminance at the end of the sleeve from which the light emerges, the LED is displaced in the sleeve by a precise measuring device lengthwise until the luminance at the end of the sleeve from which the light emerges corresponds exactly to a predetermined value. The precise measuring device can be, for example, a calibrated V(L) photocell that measures the luminance of the LED.

In this fashion, conventional LEDs with luminance values set with relatively coarse tolerance can be converted into components with very similar luminance. The elements can then be installed for example in hemispherical perimeters, whereby subsequent replacement of individual components poses no difficulties as far as variations in luminance are concerned.

In order to make the LEDs displaceable against friction in the sleeves, while holding them securely, the sleeves can be provided with projections or beads running lengthwise, said projections or beads being dimensioned so that they are elastically deformed by the LED.

The diffusing disc provided at the end of the sleeve from which the light emerges can be connected directly with the sleeve, but is can also be mounted with the aid of a cap which fits over the outside of the sleeve. The cap may be glued or screwed to the sleeve. In addition, the cap can be provided externally with mounting elements to hold the assembly at the point where it is to be installed. The end of the cap can be designed to suit the specific application. For example, for opthalmic testing equipment the cap may be made to closely match the shape and color of the viewing surface of a hemispherical perimeter, so that nonluminous stimuli will be scarcely perceptible to the viewer.

These and further objects, features and advantages of the present invention will become more obvious from the following description when taken in connection with the accompanying drawing which shows, for purposes of illustration only, a single embodiment in accordance with the present invention.

DETAILED DESCRIPTION OF THE PREFERRED EMBODIMENT

Figure 1:
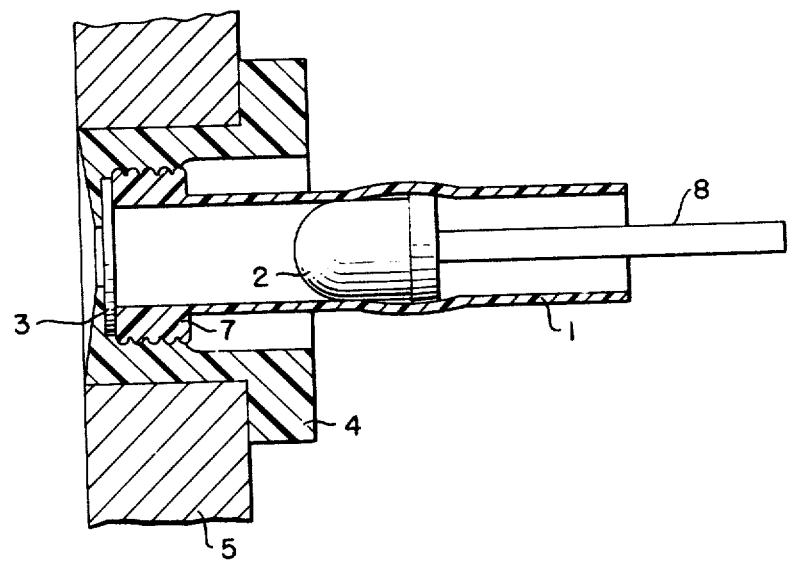
FIG. 1 is a lengthwise section through a preferred embodiment in accordance with the invention.

In FIG. 1, a sleeve 1 is visible, into which sleeve an LED 2 has been inserted. The sleeve 1 is deformed elastically in the vicinity of LED 2. A diffusing disc 3 is provided at the end of sleeve 1 from which the light emerges, said disc being held in place by a cap 4, said cap being in turn screwed onto threads 7 of sleeve 1. The outside surface of cap 4 is shaped to fit, for example, a hemispherical perimeter 5 such as that shown in FIG. 1.

Figure 2:
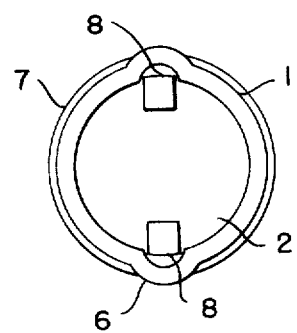
FIG. 2 is a cross section through a sleeve of the FIG. 1 embodiment.

FIG. 2 is a cross section through sleeve 1 of FIG. 1 at the area containing LED 2. Beads 6, running the length of sleeve 1, provide a firm seat for the radially extending portions of LED 2 and together with the elasticity of the sleeve as a whole enable the LED to be displaced to adjust the effective luminance thereof and then hold same in place once adjusted.

The beads 6, in the illustrated embodiment are formed of one material with the body of sleeve 1 and the radially extending portions 8 are the electrical connectors of the LED.

From the foregoing it can be appreciated that the present invention eliminates the ned for picking and choosing between numerous LEDs to obtain several that are sufficiently of the same luminance to be suitable for use together in an instrument, such as perimetric ophthalmic testing equipment, that requires LEDs of closely matched luminance, while still enabling the use of LEDs that are conventionally produced within normal manufacturing tolerances due to its ability to have the effective luminance of the LEDs upon disc 3 accurately adjusted.

While we have shown and described on embodiment in accordance with the present invention, it is understood that the same is not limited thereto but is susceptible of numerous changes and modifications as known to those skilled in the art and we therefore do not wich to be limited to the details shown and described herein but intend to cover all such changes and modifications as are encompassed by the scope of the appended claims.

We claim:

1. Method of using mass-produced light-emitting diodes of a predetermined luminance in instruments requiring a precise luminance value comprising the steps of disposing a light-emitting diode (LED) in a lengthwise adjustable manner within a sleeve, closing said sleeve with a light diffusing disc at an end thereof from which the light from the LED is intended to emerge, and displacing the LED, within the sleeve in such manner that a precisely defined luminance appears at the diffusing disc.

2. Method according to claim 1, wherein said disposing step is performed by inserting said LED into said sleeve so as to be retained therein by localized elastic deformation of the sleeve in an area of contact between said LED and said sleeve, said sleeve being formed of an elastic plastic material.

3. Light-emitting diode arrangement for adapting a mass-produced light-emitting diodes (LED) for use in instruments requiring a precise luminance value comprising a sleeve, a LED disposed within said sleeve in a lengthwise adjustable manner and a light diffusing disc mounted closing said sleeve at an end thereof from which light from the LED is intended to emerge, said LED being displaceable within said sleeve in such a manner that a precisely defined luminance appears at the diffusing disc.

4. Light emitting diode arrangement according to claim 3, wherein said sleeve is made of an elastic plastic.

5. LED arrangement according to claims 3 or 4, wherein the sleeve is provided with lengthwise beads, said beads being elastically deformed by the LED in the vicinity of the latter.

6. LED arrangement according to claim 5, wherein electrical connectors of the LED are received in said beads.

7. LED arrangement according to claim 3, wherein the diffusing disc is disposed between the sleeve and a cap fitting over the latter.

8. LED according to claim 7, wherein the cap is provided as a means for mounting the arrangement in the spherical surface of a perimeter of an opthalmic instrument.

9. LED according to claim 8, characterized by the fact that the end of the cap largely matches the shape and color of the spherical surface.